United States Patent [19]

Foulks, Jr.

[11] 4,107,115

[45] Aug. 15, 1978

[54] SOAPS AND ESTER-SOAPS OF α-OLEFIN DERIVED HIGH MOLECULAR WEIGHT ACIDS AS LUBRICANTS FOR THERMOPLASTIC POLYMERS

[75] Inventor: Harold C. Foulks, Jr., Newport, Ky.

[73] Assignee: Emery Industries, Inc., Cincinnati, Ohio

[21] Appl. No.: 602,328

[22] Filed: Aug. 6, 1975

Related U.S. Application Data

[62] Division of Ser. No. 535,603, Dec. 23, 1974, Pat. No. 4,029,682.

[51] Int. Cl.$^2$ .......................... C08K 5/09; C08K 5/11; C08L 27/06
[52] U.S. Cl. ............................ 260/23 XA; 106/171; 106/178; 252/17; 252/35; 260/28.5 D; 264/211; 264/300
[58] Field of Search ....... 260/23 XA, 28.5 D, 31.2 R, 260/410.6, 410.7, 413 HC, 414; 106/171, 178; 264/211, 300; 252/17, 37, 35

[56] References Cited

U.S. PATENT DOCUMENTS

| | | |
|---|---|---|
| 3,640,828 | 2/1972 | Brotz et al. ............................ 252/17 |
| 3,691,219 | 9/1972 | Boussely ............................ 260/31.6 |
| 3,928,500 | 12/1975 | Kraft et al. ...................... 260/23 XA |
| 3,979,347 | 9/1976 | Brotz et al. ...................... 260/28.5 D |
| 3,981,838 | 9/1976 | Wilson ................................. 264/211 |
| 3,988,330 | 10/1976 | Foulks, Jr. et al. ............ 260/31.2 R |

*Primary Examiner*—Allan Lieberman
*Attorney, Agent, or Firm*—Gerald A. Baracka; John D. Rice

[57] ABSTRACT

Soaps and ester-soaps of high molecular weight branched- and straight-chain aliphatic monocarboxylic acids obtained from α-olefins containing 22 or more carbon atoms are useful lubricants for structural resins. High molecular weight acids useful for the preparation of the soaps and ester-soaps are obtained by the free radical addition of a short chain monocarboxylic acid to $C_{22+}$ olefin or by ozonization of the $C_{22+}$ olefin. The products of this invention provide excellent internal-external lubrication for PVC homopolymers and copolymers.

7 Claims, No Drawings

SOAPS AND ESTER-SOAPS OF α-OLEFIN DERIVED HIGH MOLECULAR WEIGHT ACIDS AS LUBRICANTS FOR THERMOPLASTIC POLYMERS

This is a division, of application Ser. No. 535,603, filed Dec. 23, 1974, now U.S. Pat. No. 4,029,682.

BACKGROUND OF THE INVENTION

To facilitate processing of most resin compositions (e.g. acrylonitrilebutadiene-styrene resins, polystyrene resins, polyamide resins and polyvinylchloride (PVC) resins) lubricants are required if useful and uniform finished products are to be obtained. Lubricants play a particularly important role in the extrusion, injection molding and blow molding of rigid PVC resin compositions.

Both internal and external lubrication is essential to maintain acceptable rheological properties of the melt throughout the processing and to obtain a useful finished product. Internal lubrication operates within the melt to reduce the melt viscosity of the polymer at the processing temperature and improve the flow characteristics of the materials so that a high output of resin is possible using a minimum amount of work and without destroying the physical properties of the resin. External lubrication is required to reduce friction and sticking at the interface between the plastic melt and the metal surfaces of processing equipment in order to obtain a consistently uniform product having a smooth finish and essentially free of surface defects.

Emphasis has recently been shifted to developing new and better lubricant compounds which meet all the lubrication requirements for processing PVC and other resins, that is, function both as internal and external lubricants. Several commercially available ester and ester-soap waxes derived from montanic acids are recommended for this purpose. Montan wax acids are mixed monocarboxylic acids obtained from lignite and typically contain from about 22 to 35 carbon atoms with the predominant acids falling in the $C_{26} - C_{32}$ carbon atom range. The bulk of these monocarboxylic acids contain an even number of carbon atoms.

SUMMARY OF THE INVENTION

Novel soaps and ester-soaps obtained from high molecular weight synthetic acids derived from α-olefins containing 22 or more carbon atoms have now been discovered. It has also quite unexpectedly been found that these products exhibit superior internal-external lubrication properties with thermoplastic resins at 0.1 to 5 phr level. Esters partially saponified with calcium are particularly useful as lubricants for PVC copolymers and homopolymers.

The soaps and ester-soaps of this invention are derived from high molecular weight monocarboxylic acids obtained by the ozonization of $C_{22+}$ α-olefins or by the free radical addition of short-chain monocarboxylic acids containing 3 to 12 carbon atoms to $C_{22+}$ α-olefins. Mixed acids useful for the preparation of the products of this invention obtained from the ozonization process contain at least 55% by weight $C_{21-35}$ acids with less than 30% by weight acids having fewer than 21 carbon atoms. These mixed acids are further characterized by having a ratio of odd to even carbon content acids in the $C_{21-35}$ range between about 1.5:1 and 10:1 and, more preferably, from 1.75:1 to 4:1. Especially useful products are obtained with mixed acids containing more than 70 wt. % $C_{21-35}$ acids and less than 20 wt. % acids having fewer than 21 carbon atoms. Especially useful acids from the free radical addition process are obtained when the short-chain monocarboxylic acid is propionic acid. Soaps of the above-identified high molecular weight monocarboxylic acids include those obtained with alkali metals, alkaline earth metals, amphoteric metals and heavy metals. The insoluble metal soaps of lithium, calcium, barium, magnesium, zinc or tin and combinations thereof are especially useful for this invention. Ester-soaps obtained by the partial saponification of esters derived from aliphatic hydroxylic compounds containing 2 to 25 carbon atoms and, more preferably, 2 to 12 carbon atoms are also prepared. The ester soaps typically have metal contents in the range 0.5 to 2.5 wt. %. Products of this invention which are especially useful as lubricants for PVC homopolymers and copolymers are obtained by the partial saponification with lithium, calcium, barium, magnesium, zinc or tin and mixtures of these metals of esters derived from polyols or ether-polyols selected from the group consisting of ethylene glycol, neopentyl glycol, mono-, di-, and tripentaerythritol or mono-, di-, tri- and tetraglycerol. These ester-soaps preferably contain from about 1 to 2% by weight of the metal, have acid values less than 30 and melt in the range 50°—120° C.

DETAILED DESCRIPTION

The present invention relates to useful soaps and ester-soaps of high molecular weight aliphatic monocarboxylic acids which can be either straightor branched-chain. The high molecular weight monocarboxylic acids employed are obtained from alpha-olefins containing 22 or more carbon atoms or mixtures of said alpha-olefins (hereinafter referred to as $C_{22+}$ α-olefins). Small amounts of olefins containing less than 22 carbon atoms may be present in the olefin mixture, however, for best results the amount should not exceed 10% by weight of the total olefins, and more typically will be less than 5 wt. %. There may also be present some internal (non-vinyl) olefins, however, olefins of the type $>CH=CH_2$ should comprise at least 55% and, more preferably, will be greater than 70 wt. % of the olefin feed.

Alpha-olefins satisfying the above requirements useful for the preparation of the high molecular weight monocarboxylic acids are obtainable by the polymerization of ethylene. Reactions, referred to as chain growth reactions, where ethylene is added to an aluminum alkyl and inserted between the aluminum and one of the alkyl groups are practiced commercially and described in the literature. Alpha-olefins of predetermined average size are obtained by terminating the growth reaction when the required amount of ethylene has been added and then displacing the long alkyl group. The length of the alkyl group will be dependent on the reaction conditions employed and the ethylene charge. Numerous variations of these processes are possible to shift the α-olefin distribution and are within the skill of the art. Where olefins having a narrow molecular weight distribution are desired it may be necessary to fractionally distill, solvent extract or otherwise treat the resulting olefin products prior to conversion of the high molecular weight acids. To obtain the acids from which the soaps and ester-soaps of this invention are derived, the olefin will preferably contain 90% by weight or more olefins having 22 or more carbon atoms ($C_{22+}$ olefins). Excellent results are obtained from soap and ester-soap products derived from olefins containing 70% by weight or more olefins having 30 or more carbon atoms ($C_{30+}$ olefins).

Employing the above-described alpha-olefins, the high molecular weight monocarboxylic acids useful in the preparation of the products of this invention are obtained either (a) by the high-temperature ozonization of the olefin or (b) by the free-radical addition of a short-chain monocarboxylic acid to the olefin. Both these reactions are described in the literature.

The ozonization of high molecular weight alpha-olefins at elevated temperatures is described in copending application Ser. No. 361,205 filed May 17, 1973 now abandoned, and is incorporated herein by reference. In this process high molecular weight olefins or olefin mixtures are contacted with ozone in a suitable participating reaction medium, preferably at a temperature above the titering point of the olefin/solvent reaction mixture, and then oxidatively cleaved to obtain high molecular weight monocarboxylic acids. In general the reaction procedure involves distinct steps of ozonization followed by scission and oxidation of the formed ozonides.

The first step of the process comprises reacting the olefin or olefin mixture with ozone. It is preferable in carrying out the ozonization to mix the ozone with a carrier gas. Excellent results are obtained when the carrier gas is oxygen or a mixture of oxygen with air or carbon dioxide and when the gas mixture contains from about 0.1 to about 15% by weight ozone and more preferably from about 1 to 5% ozone. The olefin is contacted with the ozone in a suitable reactor or absorber to obtain the olefin ozonide. Olefin and solvent may be fed to the reactor separately or may be combined in a mixing tank and this mixture charged.

A stoichiometric amount of ozone is generally employed if efficient contact of olefin and ozone is maintained, however, in certain systems, particularly batch processes, it may be desirable to add a slight excess of ozone to insure that all of the olefin has been converted to ozonide. Participating solvents, which are essential to the safe and efficient conduct of the process, are monocarboxylic acids containing from about 4 to about 13 carbon atoms. Pelargonic acid and mixtures of acids containing 50% or more pelargonic acid are especially useful participating solvents. In conducting the process the weight ratio of the olefin to participating solvent may range from about 2:1 to about 1:10 with best results being obtained at weight ratios between about 1:1 and 1:3. The olefin and participating solvent may be combined prior to contacting with the ozone or at least part of the solvent may be added continuously or incrementally at any stage prior to the oxidation and scission step. The temperature at which the ozonization is conducted is also important and should be maintained above about 50° C and preferably above the titering point of the reaction mixture. Temperatures in the ozonization step will therefore usually range between about 60° C and about 85° C, however, they may go as high as 100° C.

The olefin ozonide formed during the ozonization step is next reacted with oxygen under conditions which promote scission and oxidation of the ozonide to the acid products. The scission and oxidation steps may be conducted simultaneously or as separate and distinct operations. This is achieved in conventional equipment employing either batch or continuous procedures, the only requirement being that the olefin ozonide be intimately mixed with oxygen and some means provided for temperature control. The usual temperatures employed in the scission and oxidation steps of the process range between about 75° and 145° C. If distinct steps are employed for the scission and oxidation the same temperatures may be employed, however it is more customary to conduct the oxidation at slightly higher temperatures than the scission. Temperatures between about 85° and 105° C are normally employed to cleave the olefin ozonides whereas it is preferred that the oxidation be conducted at temperatures between about 100° and 125° C. Uniform and controllable scission and oxidation are obtained when these temperature limits are observed.

An amount of gaseous oxygen sufficient to completely oxidize the ozonide is required. While pure oxygen may be advantageously employed other oxygen-containing gases such as mixtures of oxygen with argon, helium, neon or nitrogen may also be used for this purpose, however, the gas mixtures should contain at least 20% by weight oxygen. An amount of oxygen ranging from about 1 to about 4 moles of oxygen per mole of olefin is used but larger amounts may be employed, as desired, to speed the process, insure complete oxidation and improve yields. The efficiency of contacting the materials is important since the time required for splitting and oxidizing the ozonides is highly dependent thereon. In most instances this phase of the reaction is substantially complete in from about ½ to about 20 hours.

Catalysts are not necessary to bring about the scission and oxidation of the ozonide, however, they are usually desirable to accelerate these reactions. Synergistic combinations of catalytic agents may be used. Useful materials which may be added to the ozonide mixture prior to subjecting it to oxidation and which serve as catalytic agents include the alkali and alkaline earth metal hydroxides and various metal compounds including salts of Group VIII metals, preferably, iron, cobalt and nickel, and other compounds of these and other metals such as manganese. The chlorides, sulfates and carboxylates of these metals are useful as are the oxides and hydroxides. The metal compounds may be used individually or a combination of two or more metal compounds may be useful. The amount of the total catalyst will range from about 0.01 to about 2% by weight of the total reaction mixture.

Employing olefin feeds as described above in the ozonization process of U.S. application Ser. No. 361,205, the resulting straight-chain mixed acids will generally contain less than 30 weight percent acids having fewer than 21 carbon atoms. The bulk of the mixed acids contain 21 or more carbon atoms with $C_{21-35}$ acids constituting 55% by weight or more of the mixed monocarboxylic acid product with less than 20% by weight acids having greater than about 35 carbon atoms. Most often, particularly when $C_{30+}$ olefins are employed, the acid compositions will contain less than about 20 weight percent acids having fewer than 21 carbon atoms, greater than 70 weight percent $C_{21-35}$ acids and less than about 10% acids containing more than 35 carbon atoms. The ratio of odd carbon content acids to even carbon content acids in the $C_{21-35}$ range is between 1.5:1 and 10:1. This ratio is more generally from about 1.75:1 to about 4:1. The distribution of monocarboxylic acids and the ratio of the odd to even carbon content acids distinguishes the present products obtained from α-olefins from those derived from montan wax acids.

In addition to the high molecular weight acids obtained from the above-described ozonization process of $C_{22+}$ olefins, which are predominantly straight-chain acids, branched-chain high molecular weight acids obtained by the free radical addition of short-chain monocarboxylic acids to the $C_{22+}$ olefin are also useful for the production of the novel and useful soaps and ester-soaps of this invention. Acids obtained by such free radical addition reactions are predominantly α-alkyl monocarboxylic acids containing at least 25 carbon atoms. Processes for preparing such high molecular weight branched-chain acids are described in the prior art in British Pat. Nos. 960,894, 1,098,464 and 1,098,465, U.S. Pat. No. 2,823,216 as well as in other references. The α-olefin is reacted with a short-chain monocarboxylic acid containing 3 to 12 carbon atoms such as propionic, butyric, valeric, 2-ethylhexoic, pelargonic or lauric acids using a suitable free radical generating means. Excellent results are obtained with the addition of propionic acid to the α-olefin using free radical initiators such as inorganic and organic peroxides, persulfates, perborates and perchlorates. In addition to the 1:1 addition product, i.e. the α-alkyl monocarboxylic acids, other adducts are possible from the free radical reaction depending on the reactant ratio and the reaction conditions. For example, 2:1 (olefin:acid) adducts, α, α-dialkyl monocarboxylic acids, can be obtained. Similarly, some 1:2 adduct may also be formed during the reaction. It is also possible under the free radical condtions of this reaction to form dimers and possibly high oligomers of the olefin which in turn can react with short-chain acid to yield products having approximately double the molecular weight. For example, a $C_{22}$ α-olefin could form a $C_{44}$ α-olefin which in turn can react with propionic acid to yield a $C_{47}$ α-methyl branched acid. While the 1:1 adducts are the predominant species under normal reaction conditions, substantial amounts of these other adducts can be formed and are not detrimental to the formation of the products of this invention.

Useful soaps and ester-soaps prepared from the above-described high molecular weight acids include those obtained with alkali metals, alkaline earth metals, amphoteric metals and heavy metals. Illustrative metals include: lithium, sodium, potassium, beryllium, magnesium, calcium, strontium, barium, copper, silver, zinc, cadmium, mercury, aluminum, titanium, zirconium, tin, lead, antimony, bismuth, chromium, manganese, iron, nickel, cobalt and the like. Especially useful metallic soaps of the high molecular weight acids derived from $C_{22+}$ α-olefins are the insoluble metal salts of lithium, calcium, barium, magnesium, zinc or tin and mixtures thereof. Soaps and especially ester-soaps of these preferred metals are useful and effective lubricants for thermoplastic resins particularly polyvinylchloride homopolymers and copolymers. Metal contents of the products of this invention can range from low levels, about 0.1 wt. % with certain ester-soaps, to as high as 15 wt. % or more with the soaps of some of the heavier metals.

The soaps are obtained employing conventional methods of preparation which are primarily the wet (precipitation) method or dry (fusion) method. The insoluble soaps can be prepared using a double decomposition reaction by dissolving the high molecular weight monocarboxylic acid in hot water and then neutralizing with sodium hydroxide to obtain the soluble sodium salt. A solution containing the desired heavy metal is then slowly added with agitation. The insoluble metal salt immediately precipitates from solution and is recovered by filtration. This reaction is usually conducted at temperatures between about 50°–90° C. Numerous modifications of the procedure are possible depending on the solubility of the reactants, the salt to be formed, etc. as will be evident to those skilled in the art. It is also possible to directly form the soaps by heating the fatty acid in the presence of a metallic oxide, hydroxide or weakly acidic salt.

Ester-soaps of this invention are obtained by partial saponification of the acid, that is, by reacting the carboxyl groups of the high molecular weight monocarboxylic acids with a metal compound and an aliphatic hydroxylic compound containing from 2 to 25, preferably 2–12, carbon atoms and from 1 to about 10, preferably 2 to 8, primary or secondary hydroxyl groups. Useful aliphatic hydroxylic compounds include monohydric alcohols, di- and high polyhydric alcohols and ether alcohols, which can be either mono- or polyfunctional. By way of illustration useful aliphatic monohydric alcohols include ethanol, n-propanol, sec-propanol, n-butanol, t-butanol, isoamyl alcohol, n-hexanol, 2-ethylhexanol, n-octanol, isodecanol, capryl alcohol, lauryl alcohol, myristyl alcohol, cetyl alcohol, stearyl alcohol and oxo alcohols such as tridecyl alcohol, which is mainly tetramethyl-1-nonanol, and hexadecyl alcohol which is a complex mixture of primary alcohols characterized as 2,2-dialkyl ethanol wherein the alkyl groups are predominantly methyl-branched $C_6$ and $C_8$ radicals. Useful aliphatic polyols for the preparation of the ester-soaps include ethylene glycol, 1,2-propylene glycol, 1,3-propylene glycol, 1,2-butanediol, 1,3-butanediol, 1,4-butanediol, 1,5-pentanediol, 3-methyl-1,5-pentanediol, 2,3-dimethyl-2,3-butanediol, trimethylol propane, mannitol, sorbitol, glycerol, pentaerythritol and the like. Ether alcohols (intermolecular ethers formed by the condensation of two or more molecules of a polyol accompanied by the elimination of water) are also useful for the preparation of the ester-soaps of this invention. The ether alcohols can be either mono- or polyfunctional and containing from 2 up to as many as 8 condensed polyol units. Illustrative ether alcohols which can be employed are diethylene glycol, triethylene glycol, tetraethylene glycol, diethylene glycol monomethylether, diethylene glycol monoethylether, triethylene glycol monomethyl ether, butoxyethanol, butylene glycol monobutylether, dipentaerythritol, tripentaerythritol, tetrapentaerythritol, diglycerol, triglycerol, tetraglycerol, pentaglycerol, hexaglycerol, heptaglycerol, octaglycerol and the like. When polyols and ether polyols are employed it is not necessary that all the available hydroxyl groups be reacted. It is advantageous, however, when employing a polyol or mixture of polyols to have at least 50% of the available hydroxyl groups reacted.

The reaction of the metal compound and aliphatic hydroxylic compound with the high molecular weight monocarboxylic acids to obtain the ester-soaps may be conducted in a stepwise manner or all the reactants added as a unit charge. The monocarboxylic acids can first be reacted with the desired amount of metal compound to partially saponify the acid and the remaining carboxyl functionality then esterified by reaction with the hydroxylic compound. It is also possible to first esterify a portion of the carboxyl groups followed by reaction of the remaining carboxyl functionality with the metal compound. While either one of these stepwise procedures can be successfully used to yield useful ester-soaps, it is more common to carry out the reaction in a single step. In such reactions the carboxylic compound is simultaneously reacted with the metal compound and the aliphatic hydroxylic compound. The combined charge of the metal compound and hydroxylic compound should be sufficient to react with all the available carboxyl functionality.

These reactions, whether conducted in single- or multi-steps, are carried out using conventional procedures and equipment, that is, by heating the reaction mixture with or without a catalyst at a temperature from about 100° C to about 200° C while removing water of the reaction. The reactions most generally are carried out at temperatures in the range 150°–250° C. It is not essential to employ a catalyst to promote these reactions, however, acid catalysts such as sulfuric acid, phosphoric acid, alkyl and aryl sulfonic acids such as p-toluene sulfonic acid and methane sulfonic acid, as well as a variety of metal compounds including dibutyl tin oxide, tetrabutyl titanate, zinc acetate, stannous oxalate and the like can be used. If a catalyst is employed it will usually constitute about 0.1 to 1.0% by weight of the total reactant charge. Numerous modifications of the reaction procedure are possible without detracting from the desirable properties of these products as will be evident to those skilled in the art.

Especially useful products of this invention are ester-soaps obtained employing monocarboxylic acids derived from $C_{30+}$ olefins, that is, where 70% by weight or more of the olefins contain 30 or more carbon atoms. The soap portion of these preferred products is derived from a lithium, calcium, barium, magnesium, zinc or tin or mixtures of these compounds and the ester moiety is derived from a polyol or ether-polyol selected from the group consisting of ethylene glycol, neopentyl glycol, mono-, di-, or tripentaerythritol, and mono-, di-, tri- or tetraglycerol. Metal contents (weight percent) of these ester-soaps ranges from about 0.5 to 2.5% and, more preferably, will be about 1.0 to 2.0%. Particularly useful ester-soaps have acid values less than 30 and melt in the range 50°–120° C.

These ester-soaps have the ability fo function as both internal and external lubricants and satisfy the total lubricant needs of thermoplastic resins so that the incorporation of other lubricant additives is not required. The superior performance characteristics are most surprising when it is considered that similar ester-soaps obtained with naturally occuring mixed acids, such as esters of montanic acids, do not exhibit the same high degree of internal-external lubrication as the products of this invention. In addition to the unexpectedly superior internal-external lubrication the fact that these products are readily obtainable from completely synthetic sources, insuring uniformity or, where desired, controlled variation of the composition, makes them commercially attractive. The present ester-soap compositions also have other useful properties which contribute to their effectiveness and desirability as lubricants. For example, they are readily dispersible in and compatible with a wide variety of resins. They also have superior heat stabilities and are capable of withstanding rigorous processing for prolonged periods without significant decomposition, thus insuring minimal discoloration and loss of physical properties in the finished product. The ester-soaps have high melt points which is useful in maintaining a good lubricant film and their high molecular weight makes them resistant to volatilization during the processing operations. In addition to all of the above-mentioned features these ester-soaps can be utilized at very low levels resulting in considerable economic advantage to the user. This feature also minimizes the plasticization effect of the lubricant additive on the resin.

The ester-soaps are useful with numerous thermoplastic resins, however, they are particularly useful with polyvinylchloride homopolymers and copolymers. These products are effective lubricants for acrylonitrilebutadiene-styrene copolymers, polyacrylonitrile, polystyrene, polybutadiene, polyesters, polyolefins, polyvinylbutyral, cellulose acetate and the like. The ester-soaps also have application with post-chlorinated polyvinylchloride. Polyvinylchloride copolymers for which these materials function include those obtained when vinyl chloride is polymerized with vinyl acetate, vinyl bromide, vinyl propionate, vinyl butyrate, vinylidene chloride, methylmethacrylate, methylacrylate, 2-ethylhexylacrylate, acrylonitrile, methacrylonitrile styrene and the like, or any combination of two or more of these comonomers. The ester-soap products are especially useful with polyvinylchloride resins having vinyl chloride contents above about 50 percent by weight. The amount of ester-soaps employed to lubricate the resins will vary between about 0.1 part and about 5 parts per 100 parts by weight of the resin, and more usually, between about 0.2 and 2 phr.

The products of this invention are readily compatible with the aforementioned resins within the limits required for efficient internal-external lubrication. They can be incorporated into PVC or other resins using conventional means such as blending on a mill or mixing in a Banbury mixer or other internal mixer or kneading apparatus. The ester can also be dissolved or dispersed in suitable solvents and added to the resin in this manner. The lubricant can be added separately or included in a masterbatch with other compounding ingredients. The soaps and ester-soaps are readily compatible with the other compounding ingredients such as stabilizers (to protect the resins against the deleterious affects of oxygen, heat and light), pigments, dyes, fillers, plasticizers, processing aids and the like and can be used in conjunction therewith to provide formulated resins having a good balance of physical properties. The physical properties of the formulated resin can be varied considerably by manipulation of the amount and type of compounding ingredients without appreciably detracting from the internal-external lubrication properties of the present products.

The following examples illustrate the present invention more fully, however, they are not intended as a limitation on the scope thereof. In these examples all parts and percentages are given on a weight basis unless otherwise indicated.

EXAMPLE I

To obtain mixed acid products useful in the preparation of the soaps and ester-soaps of this invention equal parts of $C_{30+}$ α-olefin (Gulf $C_{30+}$ olefin fraction, m.p. 160°–167° F, containing 78 wt. % $C_{30}$ and higher olefins) and pelargonic acid were fed into the top section of a countercurrent absorber while a stream of oxygen and carbon dioxide containing approximately 1.5–2% ozone was fed into the bottom section. The rates of flow of the $O_3/O_2$ gas stream and the olefin feed were adjusted so that the $C_{30+}$ α-olefin absorbed as much ozone as possible in passing through the absorber and so that all but trace amounts of ozone were removed from the oxygen. The temperature in the absorber was maintained in the range 65°–85° C. The effluent gases were scrubbed with water to remove organic vapors and particulate matter and then passed through a catalytic furnace where organic matter was oxidized to carbon dioxide and water. The gas was then dried and recycled.

The ozonide was removed from the bottom of the absorber and passed into a decomposition vessel containing a heel of pelargonic acid, 0.25% sodium hydroxide based on weight of ozonide and previously decomposed ozonide to serve as a diluent. The decomposition vessel was maintained at a temperature of 95° C while adding oxygen containing 1% ozone and the ozonide added over a 2 hour period. When the addition was complete the decomposition was continued for 2 additional hours before transferring to an oxidation reactor. The oxidation was carried out in the presence of manganese acetate tetrahydrate (0.1% based on the $C_{30+}$ olefin) in an oxygen atmosphere. The time for oxidation was 4 hours.

The mixed oxidation product was then stirred with 0.5% phosphoric acid (75%) for 15 minutes and an activated bleaching clay (Filtrol Grade No. 1) added with additional stirring. The mass was filtered to remove the manganese salts of phosphoric acid and the filter aid and then stripped of pelargonic acid under reduced pressure using a Vigreaux column. The stripping was conducted at 230° C and during the final stages the pressure was reduced to 0.5 torr. A portion of the mixed acid product, crystallized from glacial acetic acid, was analyzed by gas-liquid chromatography of the methyl esters employing a modification of ASTM Test Method D 1983-64T. A Hewlett Packard Model 7550 chromatograph equipped with a 6 feet $\times$ ⅛ inch stainless steel column packed with 10% silicone rubber on 80-100 mesh Diatoport S was used. The instrument was programmed for an 8° C per minute temperature rise over the range 75–333° C with a helium flow of 15 mls per minute and 50 psig. The mixed acid product (equivalent weight 586; 7–8 Gardner color) had the following compositional analysis:

| Acid | WT. % |
| --- | --- |
| $C_{9-21}$ | 10.27 |
| $C_{22}$ | 3.85 |
| $C_{23}$ | 5.14 |
| $C_{24}$ | 3.26 |
| $C_{25}$ | 6.83 |
| $C_{26}$ | 3.08 |
| $C_{27}$ | 11.57 |
| $C_{28}$ | 2.83 |
| $C_{29}$ | 12.54 |
| $C_{30}$ | 1.72 |
| $C_{31}$ | 10.53 |
| $C_{32}$ | 1.29 |
| $C_{33}$ | 8.13 |
| $C_{34}$ | 0.89 |
| $C_{35}$ | 6.00 |
| $C_{36+}$ | 11.95 |
|  | 99.88 |

EXAMPLE II

A predominantly alpha-methyl branched high molecular weight monocarboxylic acid was prepared by charging a glass reactor with 200 grams of an alpha-olefin mixture containing greater than 85 wt. % $C_{22-88}$ olefins (Gulf $C_{22+}$ alpha-olefin fraction, m.p. 127° F), 326 grams propionic acid and 8 grams di-t-butyl peroxide. The system was flushed with nitrogen and a slight nitrogen flow maintained while the reaction mixture was heated at reflux for about 4 hours. At the completion of the reaction unreacted propionic acid was removed under vacuum at 200° C. 225 Grams of the $C_{25+}$ alpha-methyl monocarboxylic acid having an acid value of 48 was recovered.

EXAMPLE III

A reactor was charged with a mixture of 300 grams of the $C_{22+}$ olefin of Example II and 200 grams pelargonic acid (Emfac 1202 pelargonic acid). A stream of oxygen containing 3% ozone was continuously bubbled in below the surface of the liquid at a rate of 24 SCFH at 4 psign so that approximately 35 grams ozone was being charged per hour. The temperature of the absorber was maintained above the titering point of the reaction mixture with vigorous agitation to insure intimate contact with the ozone and the progress of the reaction followed by analyzing the off-gases. Ozonolysis was terminated when ozone absorption dropped below 15%. The ozonides were oxidatively cleaved by the dropwise addition of the ozonide mixture into a vessel containing 100 grams pelargonic acid and 0.75 grams sodium hydroxide over a period of about 90 minutes. The reaction mixture was vigorously agitated and maintained at about 95° C while bubbling in a stream of oxygen containing 1% ozone at a rate of 2.4 SCFH. When the addition was complete, stirring was continued for an additional 90 minutes while bubbling in the $O_3/O_2$ mixture. The ozone generator was then turned off. Manganese acetate tetrahydrate (1.5 gms) was added and the temperature of the reaction mixture raised to 120° C while bubbling in pure oxygen with stirring. After 3 ½ hours the oxidation reaction was complete and the mixed oxidation product was stripped of pelargonic acid by heating to 245° C while pulling a vacuum of 25 torr on the system. The mixed acid product contained approximately 80 wt. % $C_{21+}$ monocarboxylic acids.

EXAMPLE IV

The metallic soap of mixed $C_{29+}$ monocarboxylic acids obtained by the ozonization of an $\alpha$-olefin mixture containing greater than 75% by weight olefins having 30 or more carbon atoms in accordance with the procedure of Example I was prepared by double decomposition. The sodium salt of the acid was first prepared by adding 0.1 equivalent of the mixed acids (recrystallized from 5:1 methanol) to an aqueous solution containing 0.1 equivalent sodium hydroxide and maintained at 85° C. The reaction mixture was stirred at 90° C for 30 minutes and 0.1 equivalent calcium chloride dissolved in 1000 mls water added with agitation. The calcium soap immediately precipitated from solution and was recovered by filtration. After thoroughly washing with water to remove the sodium chloride the soap was dried at 65° C. The resulting soap of the mixed high molecular weight acids contained 3.4 wt. % calcium, had a negligible acid value and melted at 134°–143° C.

EXAMPLE V

Employing a procedure similar to that described in Example IV the calcium soap of a high molecular weight $\alpha$-methyl branched acid obtained by the addition of propionic acid to a $C_{30+}$ olefin mixture was prepared. 0.5 Equivalent of the high molecular weight $\alpha$-methyl branched acid was first converted to the sodium salt by neutralization with 0.5 equivalent sodium hydroxide. The sodium salt was then converted to the insoluble calcium soap by the addition of an aqueous solution containing 0.5 equivalent calcium chloride. The precipitated calcium soap was washed until there was less than 0.1% sodium chloride in the filtrate and dried at 65° C. The soap contained about 2 wt. % calcium and melted between 122°–128° C.

EXAMPLE VI

The cadmium soap of the α-methyl branched acid of Example V was prepared by melting 0.25 equivalent of the acid, adding the melt to 2 liters water maintained at 90° C and neutralizing with 0.25 equivalent sodium hydroxide. 0.25 Equivalent cadmium chloride was then added to form the insoluble soap. The cadmium soap, after washing and drying, melted at 82°–85° C.

EXAMPLE VII

The mercury soap of the mixed acids of Example I was prepared by dissolving 135.5 grams of the acid in warm water, neutralizing with 10 grams sodium hydroxide and then adding 67.9 grams $HgCl_2$. The recovered product melted at 109°–115° C.

EXAMPLE VIII

To demonstrate the ability of the products of Example IV and V to function as lubricants for PVC the calcium soaps were incorporated in the following standard pipe formulation:

| PVC resin (Geon 101-EP) | 100 parts |
|---|---|
| Tin mercaptide stabilizer | 2 parts |
| Titanium dioxide | 3 parts |
| Acrylic processing aid | 4 parts |
| Lubricant soaps | 0.5 part |

The ingredients were blended in a Henschel high speed mixer and the resin evaluated in a Brabender plasticorder — a convenient laboratory evaluation tool which measures the flow properties of the resin against time. Evaluation conditions were as follows: resin charge 55 grams; No. 6 roller head; temperature 195° C; and rotor speed 60 rpm. Test results obtained are set forth below and compared with an unlubricated control resin.

| Lubricant Soap | $T_s$ (time to start of fusion) | Torque (meter-grams) | $T_p$ (time to fusion peak) | Torque (meter-grams) |
|---|---|---|---|---|
| IV | 18.5 | 550 | 19.75 | 3100 |
| V | 31 | 600 | 34.5 | 3250 |
| None | 1.25 | 650 | 2.75 | 3800 |

It is evident from the above data that the soaps of this invention are effective lubricants for PVC and extend the fusion time of PVC resins.

EXAMPLES IX – XI

A series of ester-soaps having varying calcium contents were prepared employing the high molecular weight α-methyl monocarboxylic acid obtained by the free radical addition of propionic acid to a $C_{30+}$ olefin mixture. The ester-soaps were prepared by simultaneously reacting the monocarboxylic acid, tripentaerythritol and calcium hydroxide at 220°–230° C in the presence of 0.03 wt. % dibutyl tin oxide catalyst while removing the water of reaction. Reactant charges (in equivalents) and properties of the resulting ester-soaps were as follows:

|  | IX | X | XI |
|---|---|---|---|
| REACTANTS: |  |  |  |
| α-Methyl monocarboxylic acid | 1 | 1 | 1 |
| Tripentaerythritol | 0.75 | 0.5 | 0.25 |
| Calcium hydroxide | 0.25 | 0.5 | 0.75 |
| PROPERTIES: |  |  |  |
| Wt. % Calcium | 0.53 | 1.07 | 1.46 |
| Acid Value | 20.8 | 18.5 | 16.6 |
| Hardness | 117 | 132 | 85 |

% Calcium was determined by ashing and atomic absorption (Perkin Elmer Model 303) and hardness measured in accordance with ASTM D 1321-61T.

The ester-soap products were compounded with a typical PVC resin formulation as follows:

| PVC resin (Diamond Shamrock PVC-40; inherent viscosity 0.83) | 100 parts |
|---|---|
| Acrylic processing aid | 4 parts |
| Tin mercaptide stabilizer | 2 parts |
| Epoxidized soya | 1 part |

The resin formulations were then evaluated in the Brabender machine (56 gram sample; 160° C; No. 6 rotor head at 60 rpm). All of the ester-soaps proved to be effective lubricants for the PVC resin and extended the fusion time beyond that obtained with an unlubricated control resin and an identically formulated resin lubricated with 0.5 phr a commercially available wax product which contains about 2 wt. % Ca and is derived from montan wax and 1,3-butylene glycol. For example, the resin containing ester-soap X had not started to fuse in 20 minutes time whereas the resin containing an identical amount of the commercial product started to fuse ($T_s$) in 8 minutes at 825 meter-grams torque and had the fusion peak ($T_p$) at 10'30'' at a torque of 3300 meter-grams.

EXAMPLE XII

An ester-soap was prepared by reacting 0.45 equivalent calcium hydroxide, 0.55 equivalent glycerine and 1 equivalent α-methyl branched acids obtained by the free radical addition of propionic acid to a $C_{30+}$ olefin mixture. The reaction was conducted for about 3 hours at about 228° C in the presence of 0.03% wt. butyl titanate and 0.03% wt. $H_3PO_2$ catalysts. The ester-soap had an acid value of 15, melted at 78°–80° C and contained 0.85% calcium. The ester-soap (0.5 phr) was blended with a PVC copolymer (97 wt. % vinyl chloride/3 wt. % vinyl acetate), 2 phr tin stabilizer and 2 phr epoxidized soya and evaluated in the Brabender machine using the fusion conditions described in Example X. The resin did not fuse even after 50 minutes testing. The resin was further evaluated for dynamic thermal stability in the Brabender machine at a temperature of 195° C (other test conditions remained unchanged). After 25'30'' the initial torque rise ($T_i$) was observed but thermal degradation was not complete (as evidenced by peaking of the thermal degradation curve) even after 50 minutes testing under these severe conditions.

EXAMPLE XIII

An ester-soap was prepared using a mixture of high molecular weight acids obtained by the ozonization of a $C_{30+}$ olefin mixture. To obtain the ester-soap 2889 grams mixed acids (neutral equivalent 550), 111 grams calcium hydroxide and 95.2 grams dipentaerythritol were charged to a reactor with 0.06 wt. % catalyst and heated to about 230° C while removing the water of reaction. About 80 mls water was removed from the reaction mixture. The ester-soap contained 2 wt. % calcium, had an acid value of 20 and melted in the range of 82°–104° C. When the ester-soap was evaluated in the Brabender machine using the PVC formulation and fusion conditions of Examples IX, results were as follows:

$T_s$ 6'30" at 1000 meter-grams torque
$T_p$ 9'12" at 3050 meter-grams torque.

EXAMPLE XIV

In a manner similar to that described in Example XIII, the ester-soap of an α-methyl branched acid (neutral equivalent 1045) obtained by the free radical addition of propionic acid to a $C_{30+}$ olefin mixture was prepared by reacting 0.469 equivalent of the acid, 0.235 equivalent calcium hydroxide and 0.234 equivalent dipentaerythritol. The reaction was conducted at 225° C for 3 ½ hours using a conventional catalyst system. The ester-soap (0.95 wt. % calcium; acid value 26.1) was an effective lubricant for PVC.

EXAMPLE XV

Five equivalents mixed acid having a neutral equivalent of 556 was reacted with 3 equivalents calcium hydroxide and 2 equivalents triglycerol in the presence of a catalyst. The resulting ester soap contained 2 wt. % calcium and had an acid value of 18.6. When evaluated in the Brabender machine to determine fusion properties in accordance with the procedure and the formulations of Example IX, the following results were obtained:

$T_s$ 5'00" at 900 meter-grams torque
$T_p$ 7'30" at 3100 meter-grams torque

EXAMPLE XVI

An ester-soap of mixed $C_{29+}$ monocarboxylic acids obtained by the ozonization of α-olefin mixture containing 75% by weight or more olefins having 30 or more carbon atoms was prepared by reacting 0.55 equivalents glycerine and 0.45 equivalents calcium hydroxide with 1 equivalent of the mixed acid. The resulting product (recovered using a diatomaceous earth filter aid) melted in the range 84°–91° C and contained about 2 wt. % calcium. The ester-soap was blended with a polyvinylchloride resin (Diamond Shamrock PVC-40) in accordance with the following recipe:

| | | |
|---|---|---|
| PVC resin | 100 | parts |
| Octyl Tin stabilizer | 2 | parts |
| Epoxidized soya | 1 | part |
| Ester-soap | 0.5 | part |

The ingredients were blended in a high-speed mixer and then milled on a conventional two-roll mill at 350° F. Sheets were pressed in a 6 inch × 8 inch × 0.010 inch mold at 360° F and 500 psig for 3 minutes and 200 psig for 5 minutes. The pressed 10 mil sheets had excellent clarity. 1 inch × 1 inch Squares were stamped and arranged on eight glass trays and fitted in a rotating ferris-wheel type device in an electric oven maintained at 350° F. Samples were removed from the oven at 10 minute intervals, allowed to cool and observed for color change and other signs of polymer degradation. The test was terminated when the sample failed (blackened) or after 80 minutes. The above resin formulation showed first signs of discoloration after about 30 minutes but did not fail during the 80 minutes test period. A sample of the resin containing no ester-soap exhibited first discoloration after only 20 minutes and was completely degraded within 60 minutes.

When the resin was tested in the Brabender machine employing fusion conditions — the resin was not fused even after 60 minutes. Evaluating the resin for dynamic thermal stability in accordance with the test conditions of Example XII, the following results were obtained:

$T_i$ 17'30" at 1800 meter-grams torque
$T_{tg}$ 22'30" at 2720 meter-grams torque An unlubricated control resin gave the following results when evaluated in the Brabender for fusion and dynamic thermal stability: $T_s$ 1'18" at 1650 meter-grams torque; $T_p$ 5'45" at 4150 meter-grams torque; $T_i$ 9'00" at 2150 meter-grams torque; and $T_{tg}$ 12'24" at 3400 meter-grams torque.

The ester-soap was also tested to demonstrate its affect on extrusion rate. The PVC formulation used was as follows:

| | |
|---|---|
| PVC (Diamond Shamrock PVC-40) | 100 parts |
| Acrylic processing aid | 4 parts |
| Tin mercaptide stabilizer | 2 parts |
| Epoxidized soya | 1 part |
| Ester-soap | 0.5 part |

The resin was extruded using a Brabender machine fitted with an extrusion head Model EX-200. The extrusion was conducted at a screw speed of 40 rpm (¾ inch diameter — 20:1 L/D — 4/1 compression ratio screw; ¼ inch diameter rod die). Temperatures employed were: first zone 350° F; second zone 365° F; and die temperature 380° F. Results obtained for the formulated resin and an unlubricated control resin were as follows:

| Lubricant | Rate (lbs/hr) | Torque | Die Pressure (psig) |
|---|---|---|---|
| Ester-soap | 4.6 | 3600 | 1200 |
| None | 3.1 | 4800 | 2800 |

EXAMPLE XVII

To further demonstrate the superior lubricating ability of the products of this invention, two ester-soaps were prepared and evaluated in PVC with a commercially available wax ester-soap. Fusion properties were determined using the Brabender machine employing the previously set forth conditions. Product A, a product of this invention, contained about 2% by weight calcium and was obtained from 1,3-butylene glycol and a mixture of high molecular weight acids prepared in accordance with Example I. Another ester-soap prepared in accordance with this invention, identified as B, was the calcium soap (2 wt. % Ca) of the same mixed acid and a 50/50 mixture of ethylene glycol and 1,3-butylene glycol. The commercially available ester-soap employed for comparison was the calcium (2 wt. %) soap of montan wax acids and a glycol, primarily 1,3-butylene glycol. Ester-soaps A and B and the commercial ester-soap were incorporated into the PVC formulation of Example XVI at a 0.5 phr level with the following results:

| Lubricant | $T_s$ | Torque | $T_p$ | Torque |
|---|---|---|---|---|
| A | 18'00" | 600 | 22'15" | 3600 |

-continued

| Lubricant | $T_s$ | Torque | $T_p$ | Torque |
|---|---|---|---|---|
| B | 15'15" | 750 | 20'00" | 3000 |
| Commercial Wax | 9'00" | 800 | 11'30" | 3250 |
| None | 1'00" | 1720 | 2'45 | 4200 |

The above data clearly points out the unexpected improvement obtained with the ester-soaps of this invention.

The soaps and ester-soaps of this invention, in addition to functioning as lubricants for thermoplastic resins, also find use in numerous other applications where either synthetic or natural waxes are typically used. For example, the present products are useful as slip and antiblock agents. These materials can also be utilized in a wide variety of polishes such as shoe polish, floor polish and automobile polish. To demonstrate this, an ester-soap prepared by the reaction of 0.5 equivalents glycerine and 0.5 equivalents lithium carbonate with 1 equivalent mixed acids (neutral equivalent 524) was employed in the preparation of a shoe polish. 4.5 Parts of the ester-soap (acid value 24), 1.5 parts micro-crystalline wax (Petrolite C-1035), 3 parts carnanba wax (North Country No. 3) and 21 parts paraffin were melted at 110° C and a 50° C solution of 70 parts turpentine and 3 parts black dye blended with the melt. This mixture was cooled with stirring to 42° C and poured into containers. The resulting polish gave a high luster shine when applied to shoes. The product also exhibited good surface gloss and solvent retention. Similar results were obtained with polishes prepared from esters of glycerine and tripentaerythritol partially saponified with calcium.

I claim:

1. A thermoplastic resin composition comprising polyvinyl chloride homopolymer or copolymer and 0.1 to 5 parts per hundred parts resin of a soap or ester-soap derived from:
   (a) a mixed, straight-chain aliphatic monocarboxylic acid obtained by the ozonization of a $C_{22+}$ α-olefin and containing less than 30% by weight acids having fewer than 21 carbon atoms, less than 20% by weight acids having greater than 35 carbon atoms and 55% by weight or more $C_{21-35}$ acids wherein the weight ratio of odd to even carbon content acids in the $C_{21-35}$ range is between 1.5:1 and 10:1;
   (b) a metal compound wherein the metal is selected from the group consisting of alkali metals, alkaline earth metals, amphoteric metals and heavy metals and;
   (c) an aliphatic hydroxylic compound having 2 to 25 carbon atoms and 1 to 10 primary or secondary hydroxyl groups;
said soaps and ester-soaps containing from about 0.1 to 15% by weight of said metal.

2. The thermoplastic resin of claim 1 wherein the mixed, straight-chain aliphatic monocarboxylic acid is obtained by the ozonization of a $C_{22+}$ α-olefin wherein at least 90% by weight of the olefins have 22 or more atoms and the metal is selected from the group consisting of lithium, calcium, barium, magnesium, zinc and tin.

3. The thermoplastic resin composition of claim 2 wherein the mixed, straight-chain aliphatic monocarboxylic acid is obtained by the ozonization of an α-olefin wherein at least 70% by weight of the olefins have 30 or more carbon atoms and the mixed acid product contains less than 20 weight percent acids having fewer than 21 carbon atoms, less than 10 weight percent acids having more than 35 carbon atoms and greater than 70 weight percent $C_{21-35}$ acids with the ratio of odd to even carbon content acids in the $C_{21-35}$ range being between about 1.75:1 and 4:1.

4. The thermoplastic resin composition of claim 3 containing about 0.2 to 2.0 phr of the ester-soap wherein the aliphatic hydroxylic compound is selected from the group consisting of ethylene glycol, neopentyl glycol, pentaerythritol, dipentaerythritol, tripentaerythritol, glycerol, diglycerol, triglycerol or tetraglycerol and the metal is calcium.

5. The thermoplastic resin composition of claim 3 containing about 0.2 to 2.0 phr calcium soap.

6. The thermoplastic resin composition of claim 4 wherein the ester-soap contains from about 0.5 to 2.5% by weight calcium.

7. The thermoplastic resin composition of claim 6 wherein the ester-soap has an acid value less than 30 and melts in the range 50°–120° C.

* * * * *